United States Patent

Bollert et al.

[11] 3,962,194
[45] June 8, 1976

[54] POLYESTERS CONTAINING STRUCTURAL UNITS DERIVED FROM PHOSPHONIC ACIDS OR ESTERE

[75] Inventors: Ulrich Bollert, Hofheim, Taunus; Hans-Jerg Kleiner, Bad Soden, Taunus; Walter Herwig, Neuenhain, Taunus, all of Germany

[73] Assignee: Hoechst Aktiengesellschaft, Frankfurt am Main, Germany

[22] Filed: Feb. 10, 1975

[21] Appl. No.: 548,828

Related U.S. Application Data

[63] Continuation of Ser. No. 380,744, July 19, 1973, abandoned.

[30] Foreign Application Priority Data

July 22, 1972  Germany............................ 2236037

[52] U.S. Cl............................ 260/75 P; 260/47 C; 260/49; 260/DIG. 24
[51] Int. Cl.² .................. C08G 63/16; C08G 63/18; C08G 63/66; C08G 63/68
[58] Field of Search ......... 260/47 C, 75 P, DIG. 24, 260/49

[56] References Cited
UNITED STATES PATENTS

| | | | |
|---|---|---|---|
| 3,139,450 | 6/1964 | Friedman............................ | 260/461 |
| 3,255,145 | 6/1966 | Graham............................ | 260/30.6 |
| 3,434,981 | 3/1969 | Baranauckas et al................ | 260/2.5 |
| 3,450,669 | 6/1969 | Nolen ................................ | 260/45.9 |
| 3,525,711 | 8/1970 | Jenkner .............................. | 260/47 |

*Primary Examiner*—Lester L. Lee
*Attorney, Agent, or Firm*—Curtis, Morris & Safford

[57] ABSTRACT

Permanently flame resistant filaments and fibers are produced from synthetic linear polyesters in which about 5 to 15 mol% of the acid component of the polyester consist of phosphinic acid structural units of the formula

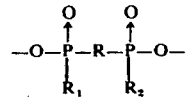

in which R, R₁ and R₂ stand for organic radicals which may contain hetero atoms, preferably halogen, oxygen or sulfur. The filaments and fibers can be well dyed deep shades and are suitable in all fields of application where textiles which are hard to inflame are desired.

4 Claims, No Drawings

POLYESTERS CONTAINING STRUCTURAL UNITS DERIVED FROM PHOSPHONIC ACIDS OR ESTERE

This is a continuation of application Ser. No. 380,744 filed July 19, 1973, and now abandoned.

The present invention relates to flame resistant filaments and fibers made from synthetic linear polyesters which have been modified with special phosphinic acids.

Filaments and fibers of linear polyesters having phosphorus-containing compounds in the polymer molecule are known. In particular, various acids of phosphorus and the derivatives thereof and among them also phosphonic and phosphinic acids have been proposed as phosphorus-containing modifying agents. In German Auslegeschrift No. 1,243,819, for example, filaments and fibers of polyesters modified with phosphonic acid esters are described. The filaments and fibers can be dyed well with basic dyestuffs and dispersion dyestuffs and have a low tendency to pilling.

In the processes disclosed in German Offenlegungsschriften Nos. 1,520,079 and 1,595,598 phosphonic acids and phosphinic acids and the derivatives thereof are added in the manufacture of fiber forming linear polyesters and incorporated into the polymer chain. In this case, too, the polyester material is modified in the first place to improve the dyeing properties of the filaments and fibers made therefrom.

It is the same with the polyester modification with bis-(p-carboxyphenyl)-phosphinic acid according to the process described in German Auslegeschrift No. 1,232,348.

It is also known that polyesters with incorporated phosphorus-containing compounds may have flame resistant properties. French Patent No. 1,196,971 provides copolyesters with phosphonic acid units which are flameproof and heat resistant. These copolyester materials can be used as flameproofing agents, adhesives, lacquers and impregnating agents for paper and textile material and as intermediates. It is not possible, however, to spin the copolyester material to filaments and fibers, as the phosphorus content causes brittleness.

To produce flame resistant or self-extinguishing filaments and fibers it has been proposed to add red phosphorus to the polyester mass prior to spinning. (Deutsche Offenlegeschrift 2,148,348). Filaments and fibers obtained in this manner have satisfactory flame resistant or selfextinguishing properties, but owing to the incorporation of red phosphorus, they do not have a white color and thus their field of appplication is limited.

It is the object of the present invention to provide permanently flame resistant polyester filaments and fibers by using a suitable modifying agent without impairing to a noteworthy degree the textile properties of the polyester filaments and fibers.

The present invention therefore comprises filaments and fibers from synthetic linear polyesters of dicarboxylic acid and diol components having phosphorus-containing chain members, which filaments and fibers are hard to inflame or selfextinguishing and have textile properties substantially equal to those of the same but unmodified polyesters. The phosphorus containing chain members incorporated into the polyester molecule in an amount of about 5 to 15 mol % of the acid component of the polyester are structural units of the formula

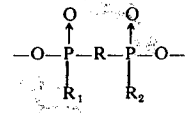

in which R represents a saturated open chain or cyclic alkylene radical having 1 to 15 carbon atoms, preferably 2 to 10 carbon atoms, or an arylene or aralkylene radical, for example $-CH_2-$, $-CH_2-CH_2-$, $-(CH_2)_3-$,

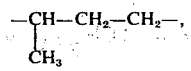

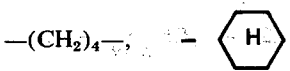

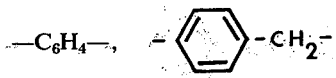

and $R_1$ and $R_2$ represent identical or different alkyl radicals having up to 6 carbon atoms, aryl or aralkyl radicals, for example $CH_3$, $C_2H_5$, n- and i-$C_4H_9$, $C_5H_{11}$, $C_6H_{13}$, $C_6H_5$ or $C_6H_5-CH_2$.

Especially preferred phosphorus-containing chain members are structural units of the formula

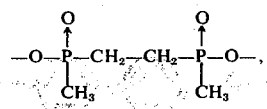

in which R represents $-CH_2-CH_2-$ and $R_1$ and $R_2$ each are $CH_3$.

The radicals R as well as $R_1$ and $R_2$ may contain 1 or several heteroatoms. The heteroatoms which are preferably contained only in the radical R are, in the first place, halogen atoms (F, Cl, Br), oxygen and sulfur, they may be bound laterally as well as in the chain, the latter being preferred. Bound in the chain means that the hetero atoms are a member of the chain consisting of carbon atoms. Because of their being monovalent, the halogen atoms cannot, of course, be bound in the chain. Preferred hetero atoms bound in the chain are therefore oxygen and sulfur. Nitrogen atoms, which are also possible as chain members in the form of —NH— or —NR' (R' being an organic radical) groups, are less suitable as in the polycondensation nitrogen compounds often give rise to undesired colorations.

The sulfur atoms can be bound in the chain in the form of sulfido, sulfinyl, or sulfonyl groups; at the chain or the aromatic ring they are preferably present in the form of sulfonate groups.

Suitable radicals R containing hetero atoms are, for example:

and as radicals R having oxygen and sulfur atoms bound in the chain the following are listed by way of example:

$- (CH_2)_3 - O - (CH_2)_3 -,$     $- (CH_2)_2 - O - (CH_2)_2 - O - (CH_2)_2 -,$ $- (CH_2)_4 - O - (CH_2)_4 -,$     $- (CH_2)_4 - S - (CH_2)_4 -,$ $- (CH_2)_4 - \underset{O_2}{S} - (CH_2)_4 -,$     $- \text{(Ph(H))} - O - \text{(Ph(H))} -,$ $- \text{Ph} - O - \text{Ph(Cl)} -,$     $- CH_2 - \text{Ph} - O - \text{Ph} - CH_2 -,$ $- CH_2CH_2 - O - \text{Ph} - OCH_2CH_2 -,$     $- \text{Ph} - S - \text{Ph} -,$ $- CH_2 - \text{Ph} - S - \text{Ph} - CH_2 -,$     $- CH_2O - \text{Ph} - OCH_2 -,$ $- \text{Ph} - SO_2 - \text{Ph} -,$     $- CH_2 - \text{Ph} - \underset{O_2}{S} - \text{Ph} - CH_2 -,$ $- CH_2CH_2 - O - \text{Ph-Ph} - OCH_2CH_2 -,$     $- CH_2 - \text{Ph} - O - \text{Ph(SO_3Na)} - CH_2 -,$ $- CH_2CH_2O - \text{Ph} - O - \text{Ph} - O CH_2CH_2 -.$ In the case of R being a saturated open chain or cyclic alkylene radical a halogen substitution is only possible if the compounds do not or to a small extent only split off hydrogen halide under the manufacturing conditions of the polyester. Suitable halogen-substituted alkylene radicals are, for example, radicals of the formula $$-CH_2-\underset{\underset{CH_2X}{|}}{\overset{\overset{CH_2X}{|}}{C}}-CH_2-$$

(in which X stands for fluorine, chlorine or bromine) or perfluorinated alkylene radicals.

The radicals $R_1$ and $R_2$ may contain hetero atoms in like manner, halogen atoms and the sulfonate group being preferred.

The linear polyesters containing the specified structural units as chain members are produced as follows: The starting materials commonly used for the manufacture of fiber-forming linear polyesters are reacted in known manner while adding prior to, during, or shortly before termination of the polycondensation a bifunctional alkylene- or arylene- or aralkylene-diphosphinic acid which may contain further hereto atoms, and/or an ester thereof with a low molecular weight alcohol preferably having of from 1 to 4 carbon atoms or with the diol forming the diol component of the polyester. The oligomers of the di-phosphinic acid diol esters may also be used.

As dicarboxylic acid components are used, either in free form or in the form of esters with low molecular weight alcohols, preferably having 1 to 4 carbon atoms (more preferably $CH_3OH$) besides terephthalic acid which is preferred, also other dicarboxylic acids, the latter preferably as cocomponents. There are mentioned by way of example isophthalic acid, 5-sulfoisophthalic acid, 5-sulfo-propoxy-isophthalic acid, naphthalene-2,6-dicarboxylic acid, diphenyl-p,p'-dicarboxylic acid, p-phenylene-diacetic acid, diphenyl oxide, p,p'dicarboxylic acid, diphenoxy-alkane-dicarboxylic acids, trans-hexahydroterephthalic acid, adipic acid, sebacic acid, 1,2-cyclobutane-dicarboxylic acid.

As diol components, besides the preferred ethylene glycol and 1,4-butane-diol, there can be used, for example, 1,3-propane-diol and the higher homologs of 1,4-butane-diol, and also 2,2-dimethyl-1,3-propane-diol, 1,4-cyclohexane-dimethanol, optionally as cocomponents.

When besides terephthalic acid other dicarboxylic acids as specified above are used as cocomponents their proportion in the total acid component should preferably not exceed substantially about 10 mol %. The same applies to the composition of the diol component. When besides ethylene glycol or 1,4-butane-diol other diols are used as cocomponents their amount should not exceed substantially about 10 mol % of the total diol component.

With the use of free dicarboxylic acids and diols the reactants are first esterified in usual manner and the reaction product is then polycondensed. When the dicarboxylic acid esters are used instead of the free dicarboxylic acids, especially the dimethyl esters, first ester interchange is brought about as usual and the reaction mixture is then polycondensed using the catalysts known in the art.

Naturally, during the course of the polyester manufacture besides the usual catalysts common additives such as cross linking agents, dulling agents, stabilizers, dyestuffs or fillers may be added.

The bifunctional alkylene- arylene- or aralkylene-diphosphinic acids possibly containing further hetero atoms, or the esters thereof added to the polyester melt prior to, during, or shortly before the termination of the polycondensation are prepared by known methods as described for example in U.S. Pat. No. 3,403,176 or J. Org. Chem, 32, pages 2172 et seq. (1967). The diphosphinic acid diol esters and the oligomers thereof are preferably prepared by the process disclosed in our copening application Ser. No. 380,743, filed July 19, 1973 and now U.S. Pat. No. 3,875,263, issued April 1, 1975, and thus with patent application Ser. No. 380,744, filed on July 19, 1973, filed concurrently herewith. When the free alkylene-, arylene, or aralkylene-phosphinic acids optionally containing further hetero atoms are used, it should be considered that they may be slightly volatile at high vacuum and high temperature so that a little loss may occur until their chemical incorporation is complete. This loss may be avoided by using corresponding esters, especially the esters with the diols used as diol component of the polyester.

The phosphorus-organic structural unit is statistically distributed in the macromolecule of the final polyester. Owing to this statistic distribution the alkylene-, arylene-, or aralkylene-diphosphinic acid units may sometimes also be bound to the ends of the macromolecules. To ensure the desired flame resistance the final polyester should contain at least about 1 % by weight of phosphorus. The flame-proofing properties are further improved if the phosphorus-containing chain members in the polyesters contain halogen atoms as hetero atoms.

The condensed polyesters are spun to filaments and fibers, drawn and after-treated in usual manner.

The filaments and fibers obtained have very good permanent flame resistant or self-extinguishing properties. They have a good degree of whiteness and can be well dyed with acid dyestuffs medium or deep shades. When the phosphorus-containing chain members additionally contain sulfonate groups, the polyesters can also be dyed with basic dyestuff. The diglycol content of the polyester is only slightly increased. The tensile strength of the fibers and filaments, the glass transition point, and the melting point approximately correspond to the values of the corresponding non-modified polyesters.

The fibers and filaments made from the modified polyesters are used in all fields of application where readily inflammable textiles and technical articles are unsuitable, for example in canvas, carpets, curtains and the like. Together with other polymers the filaments can also be used as the one component of bicomponent threads.

The following examples illustrate the invention.

EXAMPLE 1

1,000 Grams of dimethyl terephthalate (DMT) were subjected to an ester interchange reaction under nitrogen with 720 ml of ethylene glycol using 230 mg of $Mn(Ac)_2 \cdot 4 H_2O$. After termination of the methanol separation, 100 g of ethylene-di (methyl-phosphinic acid) were added at 220°C and incoporated by esterification. After the addition of 350 mg of $Sb_2O_3$ the reaction vessel was further heated while the pressure was slowly reduced so that a pressure of 1 mm of Hg was reached at an internal temperature of 250°C. The polycondensation was terminated under 0.2 mm Hg and at 270°C. The product obtained had a relative viscosity of 1.75, measured with a 1 % solution in a 3 : 2 mixture of phenol/tetrachloroethane at 25°C, second order transition temperature Tg 74°C, crystallization temperature $T_c$ 123°C, melting point 241°C, phosphorus content 2.6 %, diglycol content 1.8 %.

The modified polyester was spun from the melt under the usual conditions and the filaments were drawn in a ratio of 1 : 3.65. The filaments obtained had a strength of 3.0 g/dtex at an elongation at break of 24 %. A knitted hose was produced therefrom with which dyeing tests and a burning test were carried through.

The hose was dyed deep shades with the following acid dyestuffs:

Supranol fast red BR, Color Index Nr. 24,790
Alphanol fast blue Color Index Nr. 62,155
Lana pearl yellow 3 G Color Index Nr. 19,025.

For the burning test a piece of the knitted hose was burned on a semi-circle tester (DIN 54 331) over a carrier fabric of cotton. The flame extinguished at an angle of 100° to 110°. A comparative knitted hose made from non modified polyethylene terephthalate filaments burned completely.

EXAMPLE 2

The experiment of Example 1 was repeated with the exception that in the ester interchange reaction 5 mol % of DMT were replaced by dimethyl isophthalate. The polyester obtained had a melting point of 236°C and a relative viscosity of 1.74. A knitted hose made from filaments of the polyester extinguished on a semi-circle tester also at an angle of 100° to 110°.

EXAMPLE 3

The experiment of Example 1 was repeated with the exception that instead of ethylene-di(methylphosphinic acid) 90 grams of methylene-di(methylphosphinic acid) were used. The polycondensation product had a relative viscosity of 1.65. In the burning test a significant difference with respect to the polyester of Example 1 was not observed.

EXAMPLE 4

1,000 Grams of DMT, 1,100 g of 1,4-butane-diol and 450 mg of titanium tetraisopropylate were subjected to an ester interchange reaction under nitrogen at a temperature of from 180° to 200°C. After termination of the methanol separation the temperature was slowly raised while the reaction vessel was slowly evacuated until a pressure of 1 mm Hg had been reached at about 250°C. Next 130 g of the compound of the formula

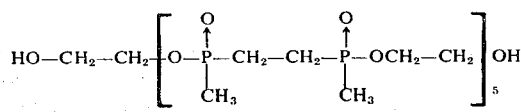

were added and the polycondensation was terminated at 260°C under a pressure of 0.1 mm Hg. The polyester obtained melted at 210° – 215°C; the phosphorus analysis indicated a content of 2.8 and 2.9 % P, the relative viscosity was 2.11. It was melt spun by extrusion, tthe spun filaments were drawn at a ratio of 1 : 3.5. The final filaments had a tensile strength of 2.7 g/dtex at an elongation at break of 25 %.

The burning properties of a knitted hose were approximately the same as those of the hose of Example 1.

EXAMPLE 5

The experiment of Example 1 was repeated, however, only half the amount of ethylene-di(methylphosphinic acid) used in said example was added, i.e. 50 g. The polycondensation product had a relative viscosity of 1.75, the second order transition temperature Tg was 80°C, the crystallization temperature $T_C$ 120°C, the melting point 254°C. The polyester had a phosphorus content of 1.3 % and a diglycol content of 0.95 %.

The result of the burning test did not differ essentially from that described in Example 1.

EXAMPLE 6

The experiment was carried out as described in Example 1, with the exception that instead of 100 g of ethylene-di(methylphosphinic acid) 100 g of phenylene-1,4-di(methylphosphinic acid) were used. The polycondensation product obtained had a relative viscosity of 1.78 and contained 2.5 % of phosphorus, the melting point was 250 - 253°C. The result of the burning test was the same as in Example 1.

EXAMPLE 7

The experiment of Example 1 was repeated using 90 g of p-xylylene-di(methylphosphinic acid) instead of the ethylene compound. The polycondensation product obtained had a relative viscosity of 1.74, it contained 2.0 % of phosphorus and had a melting point of 248° – 250°C.

The p-xylylene-di(methylphosphinic acid) was prepared from the corresponding diethyl ester obtained in known manner as follows: into 36 g of p-xylylene-di(-phosphinic acid ethyl ester) gaseous hydrogen chloride was introduced at 140°C while vigorously stirring and the temperature was gradually increased to 210°C. In a cooling trap connected in series with the reaction vessel $C_2H_5Cl$ condensed. The reaction was terminated when no more $C_2H_5Cl$ condensed. After cooling of the reaction product it was recrystallized from water. 24 Grams, 81 % of the theory, of p-xylylene-di(methylphosphinic acid) of the formula

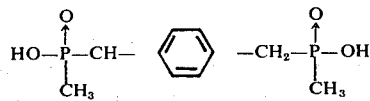

were obtained melting at 230° – 233°C. The phosphorus content was found to be 23.6 % (calculated 23.7).

EXAMPLE 8

The experiment of Example 1 was repeated with 80g of ethylene-1,2-di(phenylphosphinic acid) instead of ethylene-di-(methylphosphinic acid). The polycondensation product had a relative viscosity of 1.69, a melting point of approximately 244°C and a phosphorus content of 1.5 %. The result of the burning test corresponded to that of Example 1.

EXAMPLE 9

The experiment of Example 1 was repeated using 110 g of p,p'-bitolylene-di(methylphosphinic acid) instead of 100 g of ethylene-di(methylphosphinic acid) and a polycondensation product having a relative viscosity of 1.7, a melting point of 248° – 249°C and a phosphorus content of 1.8 % was obtained. The result of the burning test was similar to that of Example 1.

Preparation of p,p'-bitolylene-di(methylphosphinic acid)

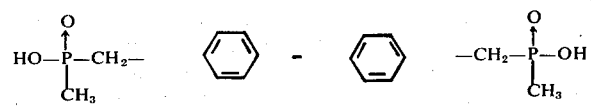

In accordance with the Michaelis-Arbusov reaction 0.5 mol of p,p'-di(chloromethyl)-biphenyl

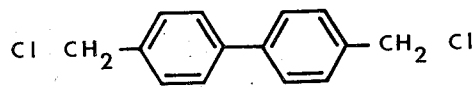

was slowly heated at 150° to 160°C under nitrogen with 1 mol of methane-phosphonic acid diethyl ester. The reaction took place with separation of $C_2H_5Cl$. It was terminated when the solution ceased to boil. The crude diphosphinic acid ester obtained was saponified with a slight excess of 20 to 30 % NaOH and after cooling the solution was acidified with dilute HCl. The p,p'-bi-tolylene-di(methylphosphinic acid) precipitated practically quantitatively. After recrystallization from glacial acetic acid it had a melting point of 291° – 292°C.

EXAMPLE 10 – 13

Preparation of further polymers the diphosphinic acid chain members of which contain additional hetero atoms The polyester modifying agents were prepared as in Example 9 with the exception that instead of p,p'-di(-chloromethyl)biphenyl the dihalide starting compounds listed in the following Table I were used. When after acidification of the reaction product saponified with NaOH (crude diphosphinic acid ester) with HCl the diphosphinic acid did not precipitate or precipitated incompletely only (in the case of purely aliphatic compounds), the acid was obtained by concentrating the solution acidified with HCl and taking up the residue with glacial acetic acid. In this process the diphosphinic acid was dissolved while NaCl separated, which was filtered off with suction and washed with a little glacial acetic acid. The glacial acetic acid solution was concentrated. From the residue the diphosphinic acid separated in the form of crystals.

Table I

| Starting dihalide | diphosphinic acid | | | yield | melting point |
|---|---|---|---|---|---|
| a) $ClCH_2$—⌬—O—⌬—$CH_2Cl$ | HO—P(=O)(CH$_3$)—CH$_2$— | ⌬—O—⌬ | —CH$_2$—P(=O)(CH$_3$)—OH | 84% | 209°C |
| b) $ClCH_2$—⌬—S—⌬—$CH_2Cl$ | HO—P(=O)(CH$_3$)—CH$_2$— | ⌬—S—⌬ | —CH$_2$—P(=O)(CH$_3$)—OH | 92% | 218–220°C |
| c) $ClCH_2$—⌬—S(O$_2$)—⌬—$CH_2Cl$ | HO'P(=O)(CH$_3$)—CH$_2$— | ⌬—S(O$_2$)—⌬ | —CH$_2$—P(=O)(CH$_3$)—OH | 75% | 290–292°C |
| d) Cl—(CH$_2$)$_4$—O—(CH$_2$)$_4$—Cl | HO—P(=O)(CH$_3$)—(CH$_2$)$_4$—O—(CH$_2$)$_4$—P(=O)(CH$_3$)—OH | | | 88% | 120.0°C |

The polyesters were prepared as described in Example 1 with the exception that instead of 100 g of ethylene-di(methylphosphinic acid) used in that example the respective di-phosphinic acid defined sub a) to d) of Table I was added. The added amount and some of the properties of the polyesters obtained are listed in the following Table II.

Table II

| Example No. | dihalide | amount diphosphinic acid, calculated on DMT (% by weight) | η rel*) | melting point | phosphorus content | diglycol content |
|---|---|---|---|---|---|---|
| 10 | a) | 10% | 1.56 | 256–257°C | 1.5% | 0.48% |
| 11 | b) | 10% | 1.58 | 255–258°C | 1.5% | 1.50% |
| 12 | c) | 9.32% | 1.63 | 252–253°C | 1.3% | 1.40% |
| 13 | d) | 10% | 1.71 | 253–254°C | 1.9% | 1.47% |

(*)measured in 1 % solutions in 3 : 2 mixtures of phenol/tetrachloroethane at 25°C The polyesters were spun into filaments and the filaments subjected to the burning test as described in Example 1. The results obtained did not differ essentially from the result of Example 1.

What is claimed is:

1. A filament or fiber manufactured by spinning a synthetic linear modified polyester, drawing and aftertreating, which comprises preparing said modified synthetic linear polyester by reacting
   a. at least one dicarboxylic acid as an acid or as an ester of a low molecular weight alcohol, said acid being suitable for the manufacture of a fiber-forming linear polyester
   b. at least one diol, said diol being suitable for the manufacture of a fiber-forming linear polyester said acid and diol being reacted by esterification or transesterification and polycondensation, while said acid and diol being reacted, adding prior to, during or shortly before termination of the polycondensation,
   c. about 5 to 15 mol percent based on the acid component, of a bifunctional alkylene-, arylene-, or aralkylene-diphosphinic acid, which may contain further hetero- and halogen atoms, and/or an ester of said diphosphonic acid of a low molecular weight alcohol or of a diol forming the diol component of said polyester, oligomer of said diphosphinic acid diol esters, or mixtures of oligomers of said diphosphinic acid diol esters with monomers of said ester of said diphosphinic acid, said bifunctional alkylene-, arylene, or aralkylene- diphosphinic acid, including said hetero- and halogen atoms, having the formula:

$$HO-\overset{O}{\underset{R_1}{P}}-R-\overset{O}{\underset{R_2}{P}}-OH$$

in which R represents a saturated open chain or cyclic alkylene, arylene or aralkylene radical, and where R may also have at least one hetero atom and/or at least one halogen atom selected from the group consisting of F, Cl, Br; $R_1$ and $R_2$ are identical or different and each represents an alkyl group having up to 6 C-atoms, an aryl group or an aralkyl group, which may contain at least one hetero atom and/or at least one halogen atom selected from the group consisting of F, Cl, and Br.

2. The filament or fiber as defined in claim 1, wherein said polyester, of which the filament or fiber is spun, has, as the component c), ethylene-(dimethyl phosphinic acid)

$$HO-\overset{O}{\underset{CH_3}{P}}-CH_2-CH_2-\overset{O}{\underset{CH_3}{P}}-OH.$$

3. The filament or fiber as defined in claim 1, wherein said polyester, of which the filament or fiber is spun, has as the radical R of the component c), a radical having as hetero atoms O or S.

4. The filament or fiber as defined in claim 1, wherein said polyester, of which the filament or fiber is spun, has as the radical R of the component c), a radical having as hetero atoms O or S bound in the chain.

* * * * *